United States Patent
Dong et al.

(10) Patent No.: US 11,890,589 B2
(45) Date of Patent: Feb. 6, 2024

(54) ALKYLATION REACTION APPARATUS, REACTION SYSTEM, AND LIQUID ACID CATALYZED ALKYLATION REACTION PROCESS

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Minghui Dong, Beijing (CN); Baoning Zong, Beijing (CN); Xuhong Mu, Beijing (CN); Yibin Luo, Beijing (CN); Hua Chen, Beijing (CN); Jinyu Zheng, Beijing (CN); Langyou Wen, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 260 days.

(21) Appl. No.: 17/433,190

(22) PCT Filed: Feb. 21, 2020

(86) PCT No.: PCT/CN2020/076136
§ 371 (c)(1),
(2) Date: Aug. 23, 2021

(87) PCT Pub. No.: WO2020/169079
PCT Pub. Date: Aug. 27, 2020

(65) Prior Publication Data
US 2022/0126252 A1    Apr. 28, 2022

(30) Foreign Application Priority Data

Feb. 21, 2019   (CN) .......................... 201910128978.9

(51) Int. Cl.
 *B01J 19/18* (2006.01)
 *B01D 3/00* (2006.01)
 (Continued)

(52) U.S. Cl.
 CPC .......... *B01J 19/0053* (2013.01); *B01D 3/009* (2013.01); *B01J 19/1806* (2013.01); *C07C 2/62* (2013.01);
 (Continued)

(58) Field of Classification Search
 CPC ................ B01J 19/0053; B01J 19/1806; B01J 2219/0004; B01J 2219/00159;
 (Continued)

(56) References Cited

U.S. PATENT DOCUMENTS 3,207,800 A   9/1965  Williamson et al.
3,281,213 A   10/1966 Waddill
(Continued)

FOREIGN PATENT DOCUMENTS

CN      2790575 Y      6/2006
CN      100348559 C    11/2007
(Continued)

*Primary Examiner* — Huy Tram Nguyen
(74) *Attorney, Agent, or Firm* — NKL Law; Allen Xue (57) ABSTRACT

An alkylation reaction apparatus has n reactors. In the n reactors, there are m reactors including the first reactor that have three reaction zones as defined below. According to the flow direction order of alkylation reaction streams, the three reaction zones are an x reaction zone, a y reaction zone and a z reaction zone respectively; based on the mixing intensity, the mixing intensity of the y reaction zone>the mixing intensity of the x reaction zone>the mixing intensity of the
(Continued)

z reaction zone, wherein $n \geq 1$ and $n \geq m$. An alkylation reaction system includes the aforementioned alkylation reaction apparatus, and a liquid acid catalyzed alkylation reaction process by using the aforementioned alkylation reaction apparatus or the aforementioned alkylation reaction system.

20 Claims, 4 Drawing Sheets (51) Int. Cl.
*B01J 19/00* (2006.01)
*C07C 2/62* (2006.01)

(52) U.S. Cl.
CPC ............ *B01J 2219/0004* (2013.01); *B01J 2219/00159* (2013.01); *B01J 2219/00761* (2013.01)

(58) Field of Classification Search
CPC .... B01J 2219/00761; B01J 2219/00033; B01J 2219/194; B01J 19/0066; B01J 14/00; B01J 19/006; B01J 19/1818; B01J 19/242; B01J 19/24; B01J 2219/00006; B01J 2219/00051; B01D 3/009; C07C 2/62; C07C 2527/054; C07C 9/16; Y02P 20/10; C10G 29/205; C10G 53/10; C10G 2300/1081; C10G 2300/1088; C10G 50/00
USPC ........................................................ 422/187
See application file for complete search history.

(56) References Cited

U.S. PATENT DOCUMENTS

| | | |
|---|---|---|
| 6,194,625 B1 | 2/2001 | Graves et al. |
| 2004/0059167 A1 | 3/2004 | Clark et al. |
| 2009/0005622 A1* | 1/2009 | Hassan ............... B01F 27/2711 585/446 |
| 2009/0005625 A1 | 1/2009 | Hassan et al. |

FOREIGN PATENT DOCUMENTS

| | | |
|---|---|---|
| CN | 101080374 B | 9/2011 |
| CN | 105018134 A | 11/2015 |
| CN | 105219428 A | 1/2016 |
| CN | 109423329 A | 3/2019 |
| EP | 0790224 A1 | 8/1997 |

* cited by examiner

ALKYLATION REACTION APPARATUS, REACTION SYSTEM, AND LIQUID ACID CATALYZED ALKYLATION REACTION PROCESS

TECHNICAL FIELD

The present invention relates to a reaction apparatus, a reaction system and an alkylation reaction process, and particularly to an alkylation reaction apparatus, a reaction system and a liquid acid-catalyzed alkylation reaction process.

BACKGROUND TECHNOLOGY

The alkylation of isoalkane with alkene, mainly isobutane with butene, is essentially an organic addition reaction of alkane molecules to alkene molecules in the presence of an acidic catalyst. Alkylation is an important process in the petrochemical industry. Iso-C8 alkane, called alkylation oil or alkylate, is produced by reacting isobutane with butenes over a strong acid catalyst. The alkylation oil has high octane number (RON 94-96), low Reid vapor pressure, extremely low sulfur content and alkene content, no benzene and aromatic hydrocarbon, and is an excellent gasoline blending component. The reformulated gasoline is used as the fuel of the gasoline engine, so that urban air pollution caused by automobile exhaust emission can be greatly mitigated. In this sense, the alkylation oil is an environmentally friendly petrochemical product.

At present, the catalysts used in the alkylation reaction in industry are mainly liquid strong acids such as concentrated sulfuric acid or hydrofluoric acid. The typical alkylation reaction process still uses a horizontal stirred tank reactor, and the alkylation reaction of isobutane and butene is a typical double liquid phase reaction, and the interphase mass transfer rate determines the macroscopic reaction rate. In such a reaction system, in the case of the sufficient dispersing and mixing of the two phases, the complete conversion of the alkene can be achieved quickly, and if the reaction time is too long, trimethylpentane (TMP) having a high octane number which is initially formed continues to contact the strongly acidic catalyst, causing the isomerization of TMP to dimethylhexane (DMH) having a low octane number. Therefore, it is difficult to achieve high conversion and high octane product with conventional stirred tank reactors.

The alkylation reaction of isoalkane and alkene belongs to an immiscible liquid-liquid two-phase reaction, and the mixing effect of the immiscible liquid-liquid two-phase has important influence on the conversion rate and selectivity of the liquid-liquid reaction. The existing liquid-liquid two-phase mixing reactor mainly comprises a stirring tank, a static mixer, an impinging stream mixer, an ejector mixer and the like.

CN2790575Y discloses a horizontal reactor in sulfuric acid alkylation process, the main body of which is a horizontal pressure vessel, and the reactor is provided with an internal circulation sleeve, a tubular heat-taking tube bundle, and a helical stirring paddle at the end enclosure. Reaction feed and recycle acid enter the suction side of the stirring paddle, reaction materials are rapidly diffused and form emulsion with the acid under the driving of the stirring paddle, and the emulsion ceaselessly circulates at high speed in the reactor and reacts. On the discharge side of the reactor, a part of the emulsion was discharged to an acid settling tank to separate the acid. The acid sinks to the bottom of the settling tank due to its higher specific gravity and then returns to the suction side of the stirring paddle. The mixing process of reactants is completed in the whole horizontal reactor, the mixing space size is the whole reactor, the time is moderately 20-30 minutes, and the method belongs to the category of macroscopic mixing. The back-mixing in this reactor is large and is not conducive to increasing the selectivity of the reaction.

U.S. Pat. No. 6,194,625B1 discloses a staged feeding alkylation reactor in which the reaction zone is divided into several zones that are connected in series and the fresh feed is divided into several streams that are introduced into each reaction zone, while the recycled acid-hydrocarbon emulsion is in a series flow and is mixed in each reaction zone by mechanical agitation. This structure overcomes the problem of large back-mixing, but is too complex. In addition, the two reactors both adopt a fixed motor to drive the stirring paddle, so that leakage is easy to generate due to poor sealing.

CN100348559C proposes an ionic liquid catalyzed alkylation reaction process and a reactor apparatus, which is to complete the liquid-liquid phase alkylation reaction of isoalkane and alkene catalyzed by ionic liquid in a supergravity rotating device. This invention provides a rotating bed reactor apparatus comprising: the reactor comprises a shell, a feed inlet and a discharge outlet are arranged on the shell, a rotary packed bed consisting of a rotor and a packing layer that is arranged in the shell, a feed pipe and a feed liquid spray head are arranged in the rotary packed bed, the rotary packed bed is positioned on the upper part of the shell, a liquid storage tank is arranged on the lower part of the shell, a stirring device is arranged in the center of the reactor and can stir reaction materials in the liquid storage tank, the liquid storage tank is connected with a feed liquid circulating pump to form a rotary bed circulating reactor, a mixer is connected at the inlet of a suction pipe of the circulating pump, an alkane/alkene feed liquid suction inlet and an ionic liquid inlet are formed in the mixer, a part of the reacted feed liquid and the ionic liquid are mixed in the mixer, the discharge outlet of the circulating pump is connected with the feed pipe of the rotary packed bed, the mixed feed liquid is conveyed to the rotary packed bed by the circulating pump for cyclic reaction, and a liquid level controller of the liquid storage tank is arranged on the shell to control the residence time of the feed liquid. The reactor with this structure can enhance the mixing between the reactants and the acid hydrocarbon emulsion, but the structure is still too complicated, and the production scale cannot be easily enlarged.

U.S. Pat. No. 3,281,213 proposes a vertical alkylation reactor, the main body of which is a riser connected to a horizontal tank, the horizontal tank is filled with an acid-hydrocarbon emulsion, isoalkane and alkene participating in the reaction are injected through a nozzle at the bottom of the riser, the acid-hydrocarbon emulsion in the horizontal tank is driven by the gravitational force caused by the injection to enter the riser together, and the reaction is carried out in the riser reactor. The top end of the riser is connected with a separation tank for separating the reaction products. The separated acid hydrocarbon emulsion circularly enters a horizontal tank at the bottom of the riser. The structure does not adopt a mechanical transmission component, and a series of problems caused by the built-in stirring paddle are solved. However, the mixing of the acid hydrocarbon emulsion with the other reactants in the riser is not satisfactory, and in addition, the entire reactor system, which uses one riser, two horizontal tanks and one downcomer, is bulky and not compact.

SUMMARY OF THE INVENTION

One of the purposes of the present invention is to provide, according to the characteristics of fast alkene reaction and slow hydrogen transfer reaction in the liquid acid catalyzed reaction of isoalkane and alkene, an alkylation reaction apparatus, which strengthens the dispersion intensity in the acid hydrocarbon emulsion during the initial reaction of alkene, intensifies the solubility of isoalkane in liquid acid, and accelerates the hydrogen transfer reaction.

The second purpose of the present invention is to provide a reaction system based on said reaction apparatus.

The third purpose of the present invention is to provide a liquid acid catalyzed alkylation reaction process based on said reaction apparatus.

One of the purposes of the present invention is realized by the following technical solution:

An alkylation reaction apparatus, which is characterized by comprising n reactors, in said n reactors, there are m reactors including the first reactor that are those having three reaction zones as defined below; according to the flow direction order of alkylation reaction streams, said three reaction zones are an x reaction zone, a y reaction zone and a z reaction zone respectively; based on the mixing intensity, the mixing intensity of the y reaction zone>the mixing intensity of the x reaction zone>the mixing intensity of the z reaction zone, wherein n≥1 and n≥m.

The second one of the purposes of the present invention is realized by the following technical solution:

An alkylation reaction system, comprising an alkylation reaction unit, a compression refrigeration unit, a reaction effluent refining unit, and a product fractionation unit, characterized in that the alkylation reaction unit comprises n reactors for the alkylation reaction, in said n reactors, there are m reactors including the first reactor that are those having three reaction zones as defined below; according to the flow direction order of alkylation reaction streams, said three reaction zones are an x reaction zone, a y reaction zone and a z reaction zone respectively; based on the mixing intensity, the mixing intensity of the y reaction zone>the mixing intensity of the x reaction zone>the mixing intensity of the z reaction zone, wherein n≥1 and n≥m.

The third one of the purposes of the present invention is realized by the following technical solution:

A liquid acid catalyzed alkylation reaction process, characterized in that the alkylation reaction of isobutane and C3-C5 alkene fractions is performed in n reactors, the inlet temperature for the first reactor is −10° C. to 20° C., in said n reactors, there are m reactors including the first reactor that are those having three reaction zones, which are an x reaction zone, a y reaction zone and a z reaction zone; an alkylation reaction raw material is distributed to said m reactors; in m reactors each provided with three reaction zones, the alkylation reaction stream firstly flows into the x reaction zone and then successively flows through the y reaction zone and the z reaction zone, based on the mixing intensity, the mixing intensity of the y reaction zone>the mixing intensity of the x reaction zone>the mixing intensity of the z reaction zone, wherein n≥1 and n≥m; the reaction stream has a residence time in the x reaction zone of 0.01-10 seconds, a residence time in the y reaction zone of 0.01-10 seconds, and a residence time in the z reaction zone of 0.1-15 minutes.

According to the characteristics of fast alkene reaction and slow hydrogen transfer reaction in the liquid acid catalyzed reaction of isoalkane and alkene, the present invention provides a combined reactor having multiple reaction zones, which firstly strengthens the dispersion intensity in the acid hydrocarbon emulsion during the initial reaction of alkene, then accelerates the hydrogen transfer reaction, and accelerates the macroscopic alkylation reaction rate, thereby improving the reaction conversion rate and the selectivity of reaction products, and meanwhile the reactor is more suitable for plant-scale reaction process.

In the present invention, by controlling different temperatures and different mixing intensities in the x, y and z reaction zones, the power consumption and the refrigerant consumption are further reduced, and accordingly the energy consumption of the apparatus is reduced.

Specifically, the present invention provides the first group of the following technical solutions:

1. An alkylation reaction apparatus, which is characterized by comprising n reactors, in said n reactors, there are m reactors including the first reactor that are those having three reaction zones as defined below; according to the flow direction order of alkylation reaction streams, said three reaction zones are an x reaction zone, a y reaction zone and a z reaction zone respectively; based on the mixing intensity, the mixing intensity of the y reaction zone>the mixing intensity of the x reaction zone>the mixing intensity of the z reaction zone, wherein n≥1 and n≥m.

2. The apparatus according to technical solution 1 of the first group, wherein n is 2, 3, 4, 5, 6, 7, 8; preferably n is 3, 4, 5, 6; more preferably n is 3 or 4, m=2 or 3.

3. The apparatus according to technical solution 1 of the first group, wherein for the reactor provided with three reaction zones, the inner diameter of z reaction zone>the inner diameter of x reaction zone>the inner diameter of y reaction zone.

4. The apparatus according to technical solution 1 of the first group, wherein the ratio of the inner diameter of the z reaction zone to the inner diameter of the x reaction zone to the inner diameter of they reaction zone, x:y:z=(1.1-1.8):1:(2-5).

5. The apparatus according to technical solution 1 of the first group, wherein the x, y and z reaction zones are provided with internal flow disturbance component(s).

6. The apparatus according to technical solution 5 of the first group, wherein the internal flow disturbance component is a static flow disturbance component or a dynamic flow disturbance component.

7. The apparatus according to technical solution 6 of the first group, wherein the static flow disturbance component is selected from Kenics, SMX, SV, SMV, SH, SK, SX, SL, Toray Hi-Type, or combinations thereof.

8. The apparatus according to technical solution 1 of the first group, wherein Said n reactors are connected in series and/or in parallel.

9. The apparatus according to technical solution 1 of the first group, wherein when n=3, m=3 or 2, the reactors are connected in series in an N-type manner; or when n=4, m=4, or 3, or 2, the reactors are connected in series in an M-type manner.

10. An alkylation reaction system, comprising an alkylation reaction unit, a compression refrigeration unit, a reaction effluent refining unit, and a product fractionation unit, characterized in that, the alkylation reaction unit comprises n reactors for the alkylation reaction, in said n reactors, there are m reactors including the first reactor that are those having three reaction zones as defined below, according to the flow direction order of alkylation reaction streams, said three reaction zones are an x reaction zone, a y reaction zone and a z reaction zone respectively, based on the mixing intensity, the mixing intensity of the y reaction zone>the mixing intensity of the x reaction zone>the mixing intensity of the z reaction zone, wherein n≥1 and n≥m.

11. The reaction system according to technical solution 10 of the first group, wherein a reaction raw material is mixed with an isobutane refrigerant obtained from the compression refrigeration unit, a recycled isobutane obtained from the product fractionation unit and a recycled hydrocarbon obtained from the reaction effluent refining unit, the mixture is cooled and used as the diluted alkylation reaction raw material; the effluent from the reaction effluent refining unit is subjected to a preliminary separation of acid hydrocarbon phases to produce a hydrocarbon phase, a majority of the resulting hydrocarbon phase is used as the recycled hydrocarbon; the product fractionation unit comprises at least one deisobutanizer, isobutane in the hydrocarbon phase of the reaction effluent is removed, the recycled isobutane, normal butane and an alkylation product are respectively obtained from the top of the deisobutanizer, the middle upper part of the deisobutanizer and the bottom of the deisobutanizer.

12. The reaction system according to technical solution 11 of the first group, wherein the effluent refining unit comprises an self-vaporization separator and a preliminary acid-hydrocarbon separator, a coalescing internal member is arranged at the upper part of the self-vaporization separator to provide a place for vaporizing butane and separating a reaction product from an acid phase, and an acid-hydrocarbon phase homogenizer is arranged at the lower part of the self-vaporization separator to ensure the stable operation of the apparatus; the preliminary acid-hydrocarbon separator is used for performing the primary separation of acid hydrocarbon phases, a majority of the separated hydrocarbon phase is recycled, a minority of the hydrocarbon phase is subjected to a further coalescence-deacidification separation in one or more customized precision coalescers.

13. The reaction system according to technical solution 10 of the first group, which further comprises an alkylation reaction raw material pretreatment unit, in which the alkylation reaction raw material is subjected to the operation of removing butadiene, light hydrocarbons, oxygen-containing compounds and water.

14. A liquid acid catalyzed alkylation reaction process, characterized in that the alkylation reaction of isobutane and C3-C5 alkene fractions is performed in n reactors, the inlet temperature for the first reactor is −10° C. to 20° C., in said n reactors, there are m reactors including the first reactor that are those having three reaction zones, which are an x reaction zone, a y reaction zone and a z reaction zone; the diluted alkylation reaction raw material is distributed to said m reactors; in m reactors each provided with three reaction zones, the diluted alkylation reaction raw material firstly flows into the x reaction zone and then successively flows through the y reaction zone and the z reaction zone, based on the mixing intensity, the mixing intensity of the y reaction zone>the mixing intensity of the x reaction zone>the mixing intensity of the z reaction zone, wherein n≥1 and n≥m; the reaction stream has a residence time in the x reaction zone of 0.01-10 seconds, a residence time in the y reaction zone of 0.01-10 seconds, and then a residence time in the z reaction zone of 0.1-15 minutes.

15. The reaction process according to technical solution 14 of the first group, wherein the diluted alkylation reaction raw material consists of a recycled isobutane, an isobutane refrigerant, a pretreated reaction raw material, and a recycled hydrocarbon, and the molar ratio of alkane to alkene thereof is 10-300:1, preferably 30-150:1, more preferably 40-100:1.

16. The reaction process according to technical solution 14 or 15 of the first group, wherein the diluted alkylation reaction raw material is equally distributed to said m reactors, or distributed to said m reactors in a gradually decreasing manner in the order of the reaction streams in the reactors.

17. The reaction process according to technical solution 14 of the first group, which further comprises, the effluent obtained from the outlet of the nth reactor is depressurized to 0.005-0.18 MPa by the coalescing internal member in the self-vaporization separator, a part of the C4 alkanes therein is vaporized and the reaction heat is taken away; the separated gas phase components are compressed and refrigerated to obtain the isobutane refrigerant, the remaining acid-hydrocarbon mixture is separated into two phases of acid and hydrocarbon in the lower part of the self-vaporization separator, the separated acid phase is recycled back to the x reaction zone of the first reactor, a majority of the separated hydrocarbon phase is sent to the raw material mixer, and a minority of the separated hydrocarbon phase is sent to the optional precision coalescer to further remove small acid droplets and acid esters in the hydrocarbon phase; in the deisobutanizer, isobutane in the hydrocarbon phase of the reaction effluent is removed, and the recycled isobutane, normal butane and an alkylation product are respectively obtained from the top of the deisobutanizer, the middle upper part of the deisobutanizer and the bottom of the deisobutanizer.

18. The reaction process according to technical solution 14 of the first group, which is suitable for the alkylation reaction of isobutane and C4 alkene.

19. The reaction process according to technical solution 14 of the first group, wherein the inlet temperature for the first reactor is −3 to 10° C.

20. The reaction process according to technical solution 14 of the first group, wherein in the x-reaction zone and in the y-reaction zone, the pressure drop is 0.05-0.5 MPa, preferably 0.1-0.3 MPa, and in the z-reaction zone, the pressure drop is 0.001-0.1 MPa, preferably 0.002-0.05 MPa.

21. The reaction process according to technical solution 14 of the first group, wherein the liquid acid is a concentrated sulfuric acid or a mixed acid mainly comprising a concentrated sulfuric acid.

22. The reaction process according to technical solution 14 of the first group, wherein the liquid acid further comprises an auxiliary agent.

23. The reaction process according to technical solution 22 of the first group, wherein the auxiliary agent is a sulfuric acid lower carbon ester.

24. The reaction process according to technical solution 22 of the first group, wherein the auxiliary agent is selected from ethyl sulfate, propyl sulfite, butyl sulfate, hexyl sulfate, or mixtures thereof.

25. The reaction process according to technical solution 24 of the first group, wherein the auxiliary agent is selected from a mixture of butyl sulfate and hexyl sulfate in a mass ratio of 1:(0.5-2).

26. The reaction process according to technical solution 22 of the first group, wherein the addition amount of the auxiliary agent is 0.001-0.1% by weight of the alkene feed.

In addition, the present invention also provides the second group of the following technical solutions:

1. An alkylation reaction apparatus, which is characterized by comprising n reactors, in said n reactors, there are m reactors including the first reactor that are those having three reaction zones as defined below; according to the flow direction order of alkylation reaction streams, said three reaction zones are an x reaction zone, a y reaction zone and a z reaction zone respectively; based on the mixing intensity, the mixing intensity of the y reaction zone>the mixing intensity of the x reaction zone>the mixing intensity of the z reaction zone, wherein n≥1 and n≥m.

2. The reaction apparatus according to technical solution 1 of the second group, wherein n is 2, 3, 4, 5, 6, 7, 8;

preferably, n is 3, 4, 5, 6;

more preferably, n is 3 or 4, m=2 or 3.

3. The reaction apparatus according to any of the previous technical solutions of the second group, wherein the reactor provided with three reaction zones has the inner diameters Rx reaction zone for the x reaction zone, Ry reaction zone for the y reaction zone and Rz reaction zone for the z reaction zone respectively, wherein Rz reaction zone>Rx reaction zone>Ry reaction zone, Preferably, the ratio of the inner diameter of the z reaction zone to the inner diameter of the x reaction zone to the inner diameter of the y reaction zone is Rz reaction zone:Rx reaction zone:Ry reaction zone=(2-5):(1.1-1.8):1.

4. The reaction apparatus according to any of the previous technical solutions of the second group, wherein internal flow disturbance component(s) is/provided in the x reaction zone, the y reaction zone, and/or the z reaction zone;

Preferably, the internal flow disturbance component is a static flow disturbance component or a dynamic flow disturbance component;

More preferably, the static flow disturbance component is selected from:

CompaX Mixer, SMI Mixer, KVM Mixer, SMV Mixer, SMX plus Mixer, SMXL Mixer, SMR Mixer, SMX Mixer, SMR Reactor, Contour Mixer, SMF Mixer, Polygard Mixer;

KM Mixer, KMX-V Mixer, HEV Mixer, UltraTab Mixer, WVM Mixer;

SV, SH, SK, SX, SL, Toray Hi-Type.

5. The reaction apparatus according to any of the previous technical solutions of the second group, wherein said n reactors are connected in series and/or in parallel;

Preferably, when n=3, m=3 or 2, the reactors are connected in series in an N-type manner; or Preferably, when n=4, m=4, or 3, or 2, the reactors are connected in series in an M-type manner.

6. An alkylation reaction system comprising an alkylation reaction unit, a compression refrigeration unit, a reaction effluent refining unit, and a product fractionation unit, characterized in that, the alkylation reaction unit comprises the alkylation reaction apparatus according to any of technical solutions 1-5 of the second group.

7. The reaction system according to technical solution 6 of the second group, wherein The alkylation reaction apparatus is provided with a mixer for receiving a diluted alkylation reaction raw material, the diluted alkylation reaction raw material is obtained by mixing an alkylation reaction raw material with an isobutane refrigerant obtained from the compression refrigeration unit, a recycled isobutane obtained from the product fractionation unit and a recycled hydrocarbon obtained from the reaction effluent refining unit;

The reaction effluent is subjected to a preliminary separation of acid hydrocarbon phases in the reaction effluent refining unit, a majority of (for example more than 50 wt %, more than 60 wt %, more than 70 wt %, more than 80 wt %, more than 90 wt %, or more than 95 wt % of) the resulting hydrocarbon phase is used as the recycled hydrocarbon;

The product fractionation unit comprises at least one deisobutanizer, isobutane in the hydrocarbon phase of the reaction effluent is removed, the recycled isobutane, normal butane and an alkylation product are respectively obtained from the top of the deisobutanizer, the middle upper part of the deisobutanizer and the bottom of the deisobutanizer.

8. The reaction system according to technical solution 6 or 7 of the second group, wherein the reaction effluent refining unit comprises a self-vaporization separator and a preliminary acid-hydrocarbon separator, A coalescing internal member is arranged at the upper part of the self-vaporization separator to provide a place for vaporizing butane and separating a reaction product from an acid phase, and an acid-hydrocarbon phase homogenizer is arranged at the lower part of the self-vaporization separator to ensure the stable operation of the apparatus;

The preliminary acid-hydrocarbon separator is used for performing the primary separation of acid hydrocarbon phases, a majority of the separated hydrocarbon phase is recycled, and a minority of the hydrocarbon phase is optionally subjected to a further coalescence-deacidification separation in one or more customized precision coalescers.

9. The reaction system according to any of technical solutions 6-8 of the second group, which further comprises an alkylation reaction raw material pretreatment unit, in which the alkylation reaction raw material is subjected to the operation of removing butadiene, light hydrocarbons, oxygen-containing compounds and water.

10. A liquid acid catalyzed alkylation reaction process, characterized in that the alkylation reaction of isobutane with a C3-C5 alkene fraction, preferably isobutane with a C4 alkene, is carried out in n reactors, the inlet temperature of the first reactor is −10° C. to 20° C., preferably −3 to 10° C.;

In said n reactors, there are m reactors including the first reactor that are those having three reaction zones, which are an x reaction zone, a y reaction zone and a z reaction zone;

The diluted alkylation reaction raw material is distributed to said m reactors, preferably, the diluted alkylation reaction raw material is equally distributed to said m reactors, or is distributed to said m reactors in a gradually decreasing manner in the order of the reaction streams in the reactors;

In m reactors each provided with three reaction zones, alkylation reaction streams firstly flow into the x reaction zone and then successively flow through the y reaction zone and the z reaction zone, based on the mixing intensity, the mixing intensity of the y reaction zone>the mixing intensity of the x reaction zone>the mixing intensity of the z reaction zone, wherein n≥1 and n≥m;

The reaction stream has a residence time in the x reaction area of 0.01-10 seconds, a residence time in the y reaction area of 0.01-10 seconds, and a residence time in the z reaction area of 0.1-15 minutes.

11. The reaction process according to technical solution 10 of the second group, wherein the diluted alkylation reaction raw material consists of a recycled isobutane, an isobutane refrigerant, an optionally pretreated alkylation reaction raw material, and a recycled hydrocarbon, and the molar ratio of alkane to alkene of the diluted alkylation reaction raw material is 10-300:1, preferably 30-150:1, and more preferably 40-100:1.

12. The reaction process according to technical solution 10 or 11 of the second group, which further comprises, The reaction effluent obtained from the outlet of the nth reactor is depressurized to 0.005-0.18 MPa by the coalescing internal member in the self-vaporization separator, so that a part of the C4 alkanes in the reaction effluent is vaporized and the reaction heat is taken away;

The gas phase components are separated, and the separated gas phase components are compressed and refrigerated to obtain the isobutane refrigerant, the remaining acid-hydrocarbon mixture is separated into two phases of acid and hydrocarbon in the lower part of the self-vaporization separator, and the separated acid phase is recycled back to the x reaction zone of the first reactor, a majority of the separated hydrocarbon phase is sent to the raw material mixer, and a minority of the separated hydrocarbon phase is sent to the optional precision coalescer to further remove small acid droplets and acid esters in the hydrocarbon phase;

In the deisobutanizer, isobutane in the hydrocarbon phase of the reaction effluent is removed, and the recycled isobutane, normal butane and an alkylation product are respectively obtained from the top of the deisobutanizer, the middle upper part of the deisobutanizer and the bottom of the deisobutanizer.

13. The process according to any of technical solutions 10-12 of the second group, wherein in the x-reaction zone and in the y-reaction zone, the pressure drop is 0.05-0.5 MPa, preferably 0.1-0.3 MPa, and in the z-reaction zone, the pressure drop is 0.001-0.1 MPa, preferably 0.002-0.05 MPa.

14. The process according to any of technical solutions 10-13 of the second group, wherein the liquid acid is a concentrated sulfuric acid or a mixed acid mainly comprising a concentrated sulfuric acid, Optionally, the liquid acid further comprises an auxiliary agent, wherein the addition amount of the auxiliary agent is zero or 0.001-0.1% by weight of the alkene feed;

Preferably, the auxiliary agent is sulfurous acid lower carbon ester or sulfuric acid lower carbon ester, More preferably, the auxiliary agent is one or more of ethyl sulfate, propyl sulfite, butyl sulfate and hexyl sulfate, Most preferably, the auxiliary agent is a mixture of butyl sulfate and hexyl sulfate in a mass ratio of 1:(0.5-2).

14. The reaction process according to any of technical solutions 10-14 of the second group, wherein the inlet pressure of the first reactor is 0.3-1.5 MPa.

16. The reaction system according to any of technical solutions 6-9 of the second group, wherein The reaction effluent refining unit comprises a self-vaporization separator and a preliminary acid-hydrocarbon separator which are connected in sequence, A coalescing internal member is arranged at the upper part of the self-vaporization separator to provide a place for vaporizing butane and separating a reaction product from an acid phase; the vaporized butane is sent to a compression refrigeration unit to produce an isobutane refrigerant;

An acid-hydrocarbon phase homogenizer is arranged at the lower part of the self-vaporization separator to ensure the stable operation of the apparatus;

The preliminary acid-hydrocarbon separator is used for performing the primary separation of acid hydrocarbon phases, a majority of the separated hydrocarbon phase returns to the mixer of the diluted alkylation reaction raw material, a minority of the hydrocarbon phase is optionally subjected to a further coalescence-deacidification separation in one or more customized precision coalescers, then sent to the product fractionation unit; the separated acid phase is sent to the x reaction zone of the first reactor.

DETAILED DESCRIPTION

The present invention provides an alkylation reaction apparatus, which is characterized by comprising n reactors, in said n reactors, there are m reactors including the first reactor that are those having three reaction zones as defined below; according to the flow direction order of alkylation reaction streams, said three reaction zones are an x reaction zone, a y reaction zone and a z reaction zone respectively; based on the mixing intensity, the mixing intensity of the y reaction zone>the mixing intensity of the x reaction zone>the mixing intensity of the z reaction zone, wherein n≥1 and n≥m.

In the present invention, the mixing intensity can be expressed in terms of the average droplet diameter of the reactants in the reactor, and the smaller the average droplet diameter is, the larger the mixing intensity is. The average droplet diameter can be determined by the method described in Ye Chubao, "Study on dispersion performance of SMV-type Sulzer static mixer", Chemical Engineering, 1983, No. 1, P 51-57, wherein the average droplet diameter is in direct proportion to the structural factors of the reactor (e.g., size and internal flow disturbance component) and the apparent linear velocity of the liquid. The mixing intensity is therefore directly proportional to the structural factors of the reactor.

The average droplet diameter can also be expressed by the Sauter mean diameter. The Sauter mean diameter can be used to describe the fineness degree of the dispersed droplets or bubbles. It is defined as the diameter (d32) of a droplet, which has the following characteristics: the ratio of its volume (Vp) and its surface area (Ap) is identical to the ratio of the total volume to the total surface area of all dispersed droplets, namely:

$$d_{32} = \frac{\sum_{i=1}^{n}(n_i, d_{v,i}^3)}{\sum_{i=1}^{n}(n_i, d_{s,i}^2)} = \frac{6V_p}{A_p}$$

$$d_s = \sqrt{\frac{A_p}{\pi}}$$

$$d_v = \left(\frac{6V_p}{\pi}\right)^{1/3}$$

D32 is the Sauter Diameter, ds is the surface area equivalent diameter, and dv is the volume equivalent diameter, In the alkylation reaction apparatus of the present invention, n is preferably 2, 3, 4, 5, 6, 7, or 8; more preferably n is 3, 4, 5, or 6, most preferably n is 3 or 4 and m is 2 or 3.

For the reactor having three reaction zones, the inner diameter of the z reaction zone>the inner diameter of the x reaction zone>the inner diameter of the y reaction zone; preferably, the ratio of the inner diameter of the z reaction zone to the inner diameter of the x reaction zone to the inner diameter of the y reaction zone is x:y:z=(1.1-1.6): 1:(2-3). In the case of satisfying the inner diameter proportion relation, the inner diameter of the x reaction zone can be 50-2000 mm, preferably 100-1500 mm, the inner diameter of the y reaction zone can be 50-2000 mm, preferably 100-1500 mm; and the inner diameter of the z reaction zone can be 200-3000 mm, preferably 500-2000 mm.

The x, y and z reaction zones are provided with internal flow disturbance component(s). The internal flow disturbance component is a static flow disturbance component or a dynamic flow disturbance component. The static flow disturbance component can be a static mixer available from Sulzer Company (with reference to https://www.sulzer.com/en/products/static-mixers), a Kenics Series static mixer available from Chemineer Company (with reference to https://www.chemineer.com/products/kenics.html) and static mixers provided by domestic manufactures. Examples of the static flow disturbance components include CompaX Mixer, SMI Mixer, KVM Mixer, SMV Mixer, SMX plus Mixer, SMXL Mixer, SMR Mixer, SMX Mixer, SMR Reactor, Contour Mixer, SMF Mixer, Polygard Mixer; KM Mixer, KMX-V Mixer, HEV Mixer, UltraTab Mixer, WVM Mixer; SV, SH, SK, SX, SL, Toray Hi-Type, and mixtures thereof.

According to the alkylation reaction apparatus of the present invention, said n reactors may also be regarded as n reaction segments in a single large reactor, and three reaction zones are provided in each of m reaction segments in said n reaction segments.

Figure 2:
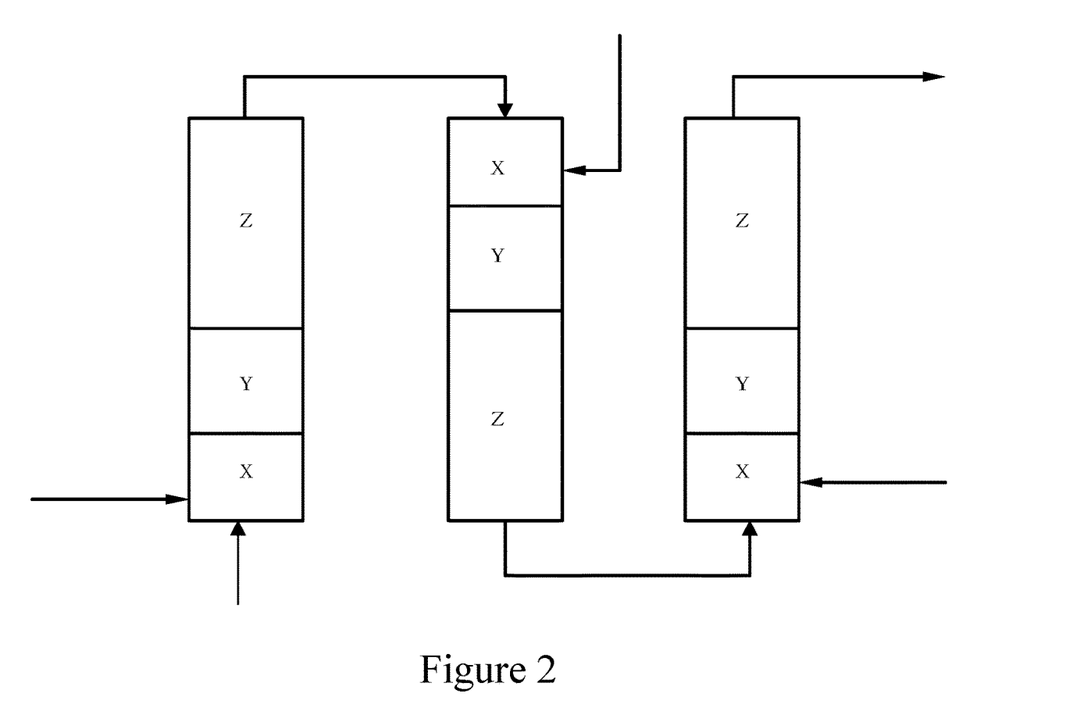
FIG. 2 is a schematic diagram of an embodiment of the reaction apparatus of the present invention.
Figure 4:
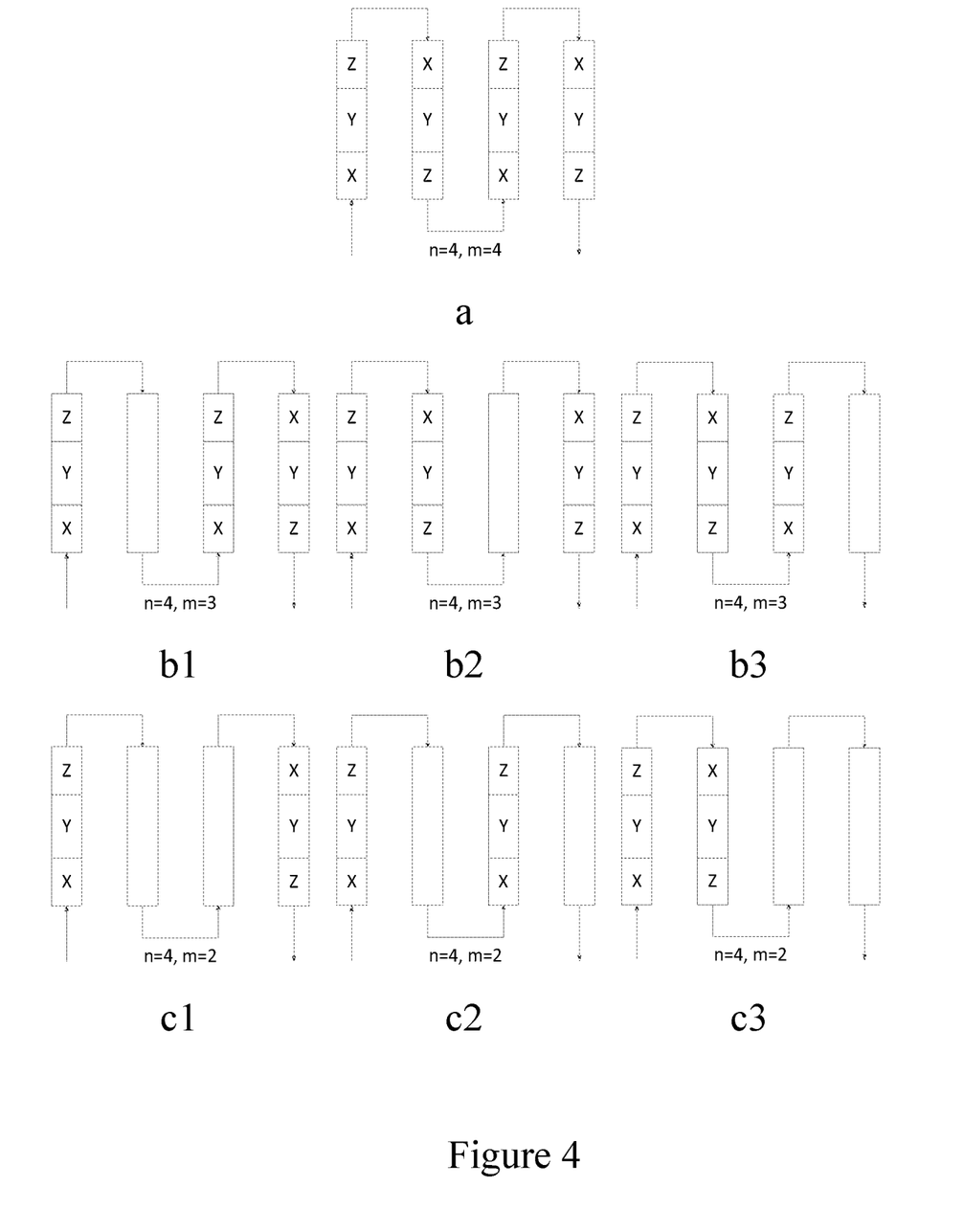
FIG. 4 is a schematic diagram of an embodiment of the reaction apparatus of the present invention.

Said n reactors are connected in series and/or in parallel. In a preferred embodiment, where n=3, m=3 or 2, the reactors are connected in series in an N-type manner (FIG. 2 shows one connection in series in the N-type manner, where n=3 and m=3); or alternatively, where n=4, m=4 or 3 or 2, the reactors are connected in series in an M-type manner (FIG. 4 shows various connections in series in the M-type manner).

The present invention also provides an alkylation reaction system, comprising an alkylation reaction unit, a compression refrigeration unit, a reaction effluent refining unit, and a product fractionation unit, characterized in that the alkylation reaction unit comprises n reactors for the alkylation reaction, in said n reactors, there are m reactors including the first reactor that are those having three reaction zones as defined below; according to the flow direction order of alkylation reaction streams, said three reaction zones are an x reaction zone, a y reaction zone and a z reaction zone respectively; based on the mixing intensity, the mixing intensity of the y reaction zone>the mixing intensity of the x reaction zone>the mixing intensity of the z reaction zone, wherein n≥1 and n≥m.

In the alkylation reaction system, an alkylation reaction raw material is mixed with an isobutane refrigerant obtained from the compression refrigeration unit, a recycled isobutane obtained from the product fractionation unit and a recycled hydrocarbon obtained from the reaction effluent refining unit; the reaction effluent is subjected to a preliminary separation of acid hydrocarbon phases in the reaction effluent refining unit to produce a hydrocarbon phase, a majority of (for example more than 50 wt %, more than 60 wt %, more than 70 wt %, more than 80 wt %, more than 90 wt %, or more than 95 wt % of) the resulting hydrocarbon phase is used as the recycled hydrocarbon and returns to the mixer of the diluted alkylation reaction raw material; the product fractionation unit comprises at least one deisobutanizer, isobutane in the hydrocarbon phase of the reaction effluent is removed, the recycled isobutane, normal butane and an alkylation product are respectively obtained from the top of the deisobutanizer, the middle upper part of the deisobutanizer and the bottom of the deisobutanizer.

The reaction effluent refining unit comprises an self-vaporization separator and a preliminary acid-hydrocarbon separator, a coalescing internal member is arranged at the upper part of the self-vaporization separator to provide a place for vaporizing butane and separating a reaction product from an acid phase, an acid-hydrocarbon phase homogenizer is arranged at the lower part of the self-vaporization separator to ensure the stable operation of the apparatus; the preliminary acid-hydrocarbon separator is used for performing the primary separation of acid hydrocarbon phases, a majority of the separated hydrocarbon phase is recycled, and a minority of the hydrocarbon phase is subjected to a further coalescence-deacidification separation in one or more customized precision coalescers.

The alkylation reaction system can also comprise an alkylation reaction raw material pretreatment unit, in which the alkylation reaction raw material is subjected to the operation of removing butadiene, light hydrocarbons, oxygen-containing compounds and water.

The present invention further provides a liquid acid catalyzed alkylation reaction process, characterized in that the alkylation reaction of isobutane and C3-C5 alkene fractions is performed in n reactors, the inlet temperature for the first reactor is −10° C. to 20° C., in said n reactors, there are m reactors including the first reactor that are those having three reaction zones, which are an x reaction zone, a y reaction zone and a z reaction zone; the diluted alkylation reaction raw material is distributed to said m reactors; in m reactors each provided with three reaction zones, alkylation reaction streams firstly flow into the x reaction zone and then successively flow through the y reaction zone and the z reaction zone, based on the mixing intensity, the mixing intensity of the y reaction zone>the mixing intensity of the x reaction zone>the mixing intensity of the z reaction zone, wherein n≥1 and n≥m; the reaction stream has a residence time in the x reaction area of 0.01-10 seconds, a residence time in the y reaction area of 0.01-10 seconds, and a residence time in the z reaction area of 0.1-15 minutes.

The diluted alkylation reaction raw material consists of a recycled isobutane, an isobutane refrigerant, optionally a pretreated reaction raw material, and a recycled hydrocarbon, and the molar ratio of alkane to alkene thereof is 10-300:1, preferably 30-150:1, more preferably 40-100:1.

Diluted alkylation reaction raw material is distributed to said m reactors, preferably the diluted alkylation reaction raw material is equally distributed to said m reactors, or distributed to said m reactors in a gradually decreasing manner in the order of the reaction streams in the reactors.

The present invention sets reaction zones with different mixing intensities according to different reaction requirements, and can control proper reaction intensity and reaction time, thereby saving the apparatus investment and the apparatus energy consumption. The mixing intensity of the reaction zone y is greater than that of the reaction zone x, so that the fed alkene can be rapidly dispersed in a short time and can be rapidly and completely reacted. The mixing intensity is examined by means of the average droplet diameter. Under the premise that the following requirements are met: the reaction zone y and the reaction zone x are both provided with the internal flow disturbance components, and the mixing intensity of the reaction zone y provided with the internal flow disturbance component is larger than that of the reaction zone x provided with the internal flow disturbance component, and meanwhile the reaction zone z is also provided with the internal flow disturbance component, and the mixing intensity of z is smaller than that of the reaction zone x, in the reaction zone y, the average droplet diameter can be independently controlled to be 10-1000 μm, preferably 50-500 μm. In the reaction zone x, the average droplet diameter can be independently controlled to be 100-5000 μm, preferably 200-1000 μm. In the reaction zone z, the average droplet diameter can be independently controlled to be 500-10000 μm, preferably 600-3000 μm.

The alkylation reaction process further comprises, the reaction effluent obtained from the outlet of the nth reactor is depressurized to 0.005-0.18 MPa by the coalescing internal member in the self-vaporization separator, a part of the C4 alkanes therein is vaporized and the reaction heat is taken away; the separated gas phase components are compressed and refrigerated to obtain the isobutane refrigerant, the remaining acid-hydrocarbon mixture is separated into two phases of acid and hydrocarbon in the lower part of the self-vaporization separator, the separated acid phase is recycled back to the x reaction zone of the first reactor, a majority of the separated hydrocarbon phase is sent to the raw material mixer, and a minority of the separated hydrocarbon phase is sent to the optional precision coalescer to further remove small acid droplets and acid esters in the hydrocarbon phase; in the deisobutanizer, isobutane in the hydrocarbon phase of the reaction effluent is removed, and the recycled isobutane, normal butane and an alkylation product are respectively obtained from the top of the deisobutanizer, the middle upper part of the deisobutanizer and the bottom of the deisobutanizer.

Generally, the purpose of most alkylation processes is to bring isoalkanes (or aromatics) and light alkenes into intimate contact with an acidic catalyst and react to form an alkylation product. Acid catalyzed alkylation of aliphatic hydrocarbons and alkenes is a well known process in the petroleum refining industry. The alkylation according to the present invention refers to a processing process of isoalkanes and alkenes under the catalysis of strong acid to produce fractions with an octane number higher than that of raw material and a boiling range of gasoline. The alkylation to which the present invention relates is generally the reaction of isobutane with a C3-C5 alkene fraction, and is particularly suitable for the reaction of isobutane with C4 alkene.

In the alkylation reaction process of the present invention, the inlet temperature of the first reactor is −10 to 20° C., preferably −2 to 10° C. The reaction pressure drops in the x reaction zone and in the y reaction zone are different from that in the z reaction zone, the reaction pressure drops in the x reaction zone and in the y reaction zone is controlled to be 0.05-0.5 MPa, preferably 0.1-0.3 MPa, and the reaction pressure drop in the z reaction zone is controlled to be 0.001-0.1 MPa, preferably 0.002-0.05 MPa.

The total mixing/contact time of the reaction streams in the x reaction zone and the y reaction zone is 0.01-10 seconds, and preferably 0.1-3 seconds. The time for mixing, contacting and reaction in the z reaction zone 0.1-15 minutes, preferably 0.5-5 minutes. In the alkylation reaction process, the volume ratio of the acid to hydrocarbon is 0.8-1.5:1, preferably 0.85-1.2:1, more preferably 0.9-1.1:1.

The liquid acid is preferably a concentrated sulfuric acid or a mixed acid mainly comprising a concentrated sulfuric acid, and more preferably a concentrated sulfuric acid with the concentration of 90%-99.2% or a mixed acid mainly comprising a concentrated sulfuric acid. Here, the concentrated sulfuric acid refers to a mixture of sulfuric acid and water, and the mixed acid mainly comprising a concentrated sulfuric acid refers to a mixture of sulfuric acid and other inorganic acids (e.g., hydrochloric acid, nitric acid, phosphoric acid, and the like) or organic acids (e.g., sulfonic acid, trifluoromethanesulfonic acid, and the like), in which the concentration of sulfuric acid is more than 50% by weight, or a mixture of sulfuric acid, water and other inorganic acids (e.g., hydrochloric acid, nitric acid, phosphoric acid, and the like) or organic acids (e.g., sulfonic acid, trifluoromethanesulfonic acid, and the like), in which the concentration of sulfuric acid is more than 50% by weight.

The liquid acid catalyst preferably further comprises an auxiliary agent. The addition of the auxiliary agent strengthens the solubility of the isoalkane in the liquid acid, accelerates the hydrogen transfer reaction and accelerates the macroscopic alkylation reaction rate, thereby improving the reaction conversion rate and the selectivity of the reaction product.

The auxiliary agent is sulfurous acid lower carbon ester or sulfuric acid lower carbon ester (herein lower carbon refers to C1-C6 alkyl), and preferably the auxiliary agent is selected from ethyl sulfate, propyl sulfite, propyl sulfite, butyl sulfate, hexyl sulfate, mixtures thereof. More preferably, the auxiliary agent is a mixture of butyl sulfate and hexyl sulfate in a mass ratio of 1:(0.5-2). The addition amount of the auxiliary agent is 0.001-0.1%, preferably 0.01-0.05% by weight of the alkene feed. The auxiliary agent can be added into the reactor independently or can be added into the reactor after being mixed with the liquid acid.

The alkylation reaction process of the present invention further comprises, a part of the C4 alkanes in the acid-hydrocarbon mixture obtained from the outlet of the nth reactor is vaporized under 0.005-0.18 MPa and the reaction heat is taken away; the separated gas phase components are compressed and refrigerated to obtain the isobutane refrigerant, the remaining acid-hydrocarbon mixture is separated into two phases of acid and hydrocarbon in the lower part of the vaporization separator, the separated acid phase is recycled back to the x reaction zone of the first reactor, a majority of the components of the separated hydrocarbon phase is mixed with the alkylation reaction raw material, and a minority of the components of the separated hydrocarbon phase is sent to the optional precision coalescer of the reaction effluent refining unit to further remove small acid droplets and acid esters.

The reaction acid phase outlet is set below the normal control liquid level in the self-vaporization separator and at the bottom of the vaporization separator, and the hydrocarbon phase outlet is preferably in the middle upper part of the liquid level and connected to the preliminary acid-hydrocarbon separator via the separated hydrocarbon phase withdrawing line. The acid phase from the lower part of the self-vaporization separator is sent to the x reaction zone of the first reactor through a recycled acid pump and via a recycled acid pipeline.

The gas component from the self-vaporization separator is compressed by a compressor and condensed and then sent into the raw material mixer. A coalescing internal member is arranged at the upper part of the self-vaporization separator to provide a place for vaporizing butane and separating a reaction product from an acid phase, and an acid-hydrocarbon phase homogenizer is arranged at the lower part of the self-vaporization separator to ensure the stable operation of the apparatus.

The acid phase from the lower part of the preliminary acid-hydrocarbon separator is recycled to the inlet of the recycled acid pump, and finally sent to the alkylation reaction unit. A majority of the hydrocarbon phase obtained by coalescing from the middle upper part of the preliminary acid-hydrocarbon separator is pressurized by a recycled hydrocarbon pump and sent through the reaction feed line to dilute the reaction raw material and control the temperature of the reaction raw material. A minority of the hydrocarbon phase obtained from the top of the preliminary acid-hydrocarbon separator is sent to the deisobutanizer via one or more precision coalescers. The gas phase isobutane separated from the top of the deisobutanizer is condensed and then used as the recycled isobutane; normal butane is withdrawn from the middle upper part of the deisobutanizer, and the alkylation product is withdrawn from the bottom of the deisobutanizer.

In the present invention, the pressure is a gauge pressure.

In the present invention, n and m, which describe the number of reaction zones, are integers.

In the present invention, the terms indicating positions such as the top (of a column), the middle upper part (of a column), the bottom (of a column); the upper part of the self-vaporization separator, the lower part of the self-vaporization separator; the lower part of the preliminary acid-hydrocarbon separator, the middle upper part of the preliminary acid-hydrocarbon separator and the top of the preliminary acid-hydrocarbon separator; the middle upper part of the liquid level and the like have conventional meanings understood by those skilled in the art, and for example, these terms are described in the order from the top to the bottom. Generally, in the length range from the bottom to the top, the middle upper portion means a portion of from 50% to 90%, the upper part means a portion of from 60% to 100%, and the lower part means a portion of from 0% to 40%; it should be noted, however, that the technical solutions of the present invention may or may not be limited by these ranges.

According to the characteristics of fast alkene reaction and slow hydrogen transfer reaction in the liquid acid catalyzed reaction of isoalkane and alkene, the present invention strengthens the dispersion intensity in the acid hydrocarbon emulsion during the initial reaction of alkene in the x and y reaction zones, accelerates the hydrogen transfer reaction in the z reaction zone, accelerates the macroscopic alkylation reaction rate, and inhibits the side reactions of the alkylation, therefore on the premise of ensuring that the product after the reaction has a high octane number, reducing the circulation quantity of isobutane in the feeding streams, reducing the energy consumption of the apparatus, and having a very strong industrial practicability.

The apparatus and the alkylation reaction process of the present invention will be described in detail with reference to the accompanying drawings, but the invention is not limited thereto.

In the examples, a C4 alkane mixed gas obtained after etherification to produce MTBE was used as the alkylation reaction raw material containing alkene (i.e. C4 liquefied gas), and the mixed raw material comprises the following components in percentage by mass: propane 0.098%, isobutane 39.36%, n-butane 13.51%, isobutene 1.39%, 1-butene 14.70%, cis-butylene 14.92%, trans-butylene 16.0%, and pentane 0.022%. In the following examples, Sauter Diameter was used as the average droplet diameter.

Example 1

This example illustrates the alkylation process and apparatus using concentrated sulfuric acid as the alkylation catalyst.

Figure 1:
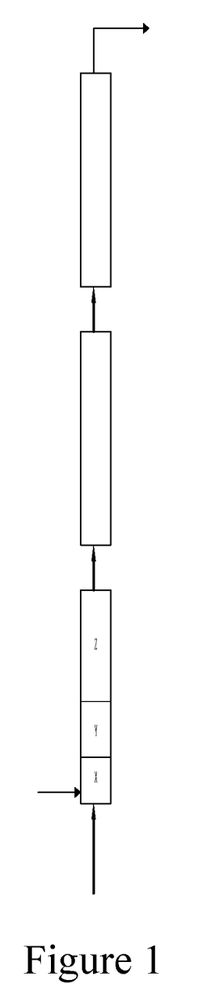
FIG. 1 is a schematic diagram of an embodiment of the reaction apparatus of the present invention.

The alkylation reaction was carried out in three reactors in series, the setup schematic is shown in FIG. 1. Three reaction zones of x, y and z were arranged in the first reactor: wherein the inner diameter of the x reaction zone was 40 mm, and Kenics type static flow disturbance component was used; the inner diameter of the y reaction zone was 25 mm, and SV type static flow disturbance component was used; the inner diameter of the z reaction zone was 100 mm, and SX type static flow disturbance component was used; the second reactor and the third reactor had no divided reaction zone therein and had inner diameters of 50 mm. Under the conditions that the medium temperature was 2° C. and the flow rate of the recycled acid was 1.2 m3/h, the mixing intensities of the x reaction zone, the y reaction zone and the z reaction zone were 275 μm, 98 μm and 1558 μm respectively, examined as the average droplet diameter.

An alkylation catalyst concentrated sulfuric acid (concentration: 98.5%, the same below) and a recycled acid were pumped into the main flow channel of the x reaction zone of the first reactor through the recycled acid pump; a recycled hydrocarbon was returned to the raw material mixer via the recycled hydrocarbon pump and fully mixed with an alkylation reaction raw material, an isobutane refrigerant and a recycled isobutane, the molar ratio of alkane to alkene was 50:1, and then the resulting mixture was sent to the x reaction zone of the first reactor, and the temperature of the first reactor was 2° C. The mixed stream resided in the x reaction zone and the y reaction zone of the first reactor for a total of 2 seconds to ensure that the alkene in the feed was completely reacted; and the reaction stream resided in the z reaction zone for 1.5 minutes to react and sequentially passed through the second reactor and the third reactor, the reaction effluent of the third reactor was depressurized and sent to the self-vaporization separator, and a part of butane vaporized in the self-vaporization separator was evaporated to take away the reaction heat timely. A majority of the acid phase separated from the self-vaporization separator was pumped back to the main flow channel of the x reaction zone of the first reactor. The gas phase component (mainly isobutane) from the upper part of the self-vaporization separator was compressed and condensed to be used as recycled isobutane. The pressure of the vaporization separator was controlled to be about 0.025 MPa, and the hydrocarbon phase separated from the self-vaporization separator was sent to the preliminary acid-hydrocarbon separator. The acid phase from the lower part of the preliminary acid-hydrocarbon separator was returned to the x reaction zone of the first reactor, and a majority of the hydrocarbon phase from the middle upper part of the preliminary acid-hydrocarbon separator was returned to the raw material mixer. A minority of the hydrocarbon phase separated from the upper part of the preliminary acid-hydrocarbon separator was subjected to a further precision coalescence and then sent to the deisobutanizer to obtain the recycled isobutane and the alkylation product respectively.

The alkylation reaction product was distilled to remove C4 components, and the obtained alkylation oil had a dry point of 195° C., an RON value of 96.5 and an MON value of 93.1.

Comparative Example 1

This comparative example illustrates the alkylation process and apparatus using concentrated sulfuric acid as the alkylation catalyst.

The same procedure was performed according to Example 1, except for the inner diameter of the y reaction zone and the flow disturbance component.

The inner diameter of the y reaction zone was 40 mm, and Kenics type static flow disturbance component was used.

The mixing intensities of the x reaction zone, the y reaction zone and the z reaction zone were 275 μm, 275 μm and 1558 μm respectively, examined as the average droplet diameter, namely the same mixing intensity was used in the x reaction zone and the y reaction zone.

The alkylation reaction product was distilled to remove C4 components, and the obtained alkylation oil had a dry point of 198° C., an RON value of 95.5 and an MON value of 92.2.

Comparative Example 2

This comparative example illustrates the alkylation process and apparatus using concentrated sulfuric acid as the alkylation catalyst.

The same procedure was performed according to Example 1, except that the mixing intensity of the y reaction zone was less than the mixing intensity of the x reaction zone.

The inner diameter of the y reaction zone was 45 mm, and Kenics type static flow disturbance component was used. The mixing intensities of the x reaction zone, the y reaction zone and the z reaction zone were 275 μm, 325 μm and 1558 μm respectively, examined as the average droplet diameter.

The alkylation reaction product was distilled to remove C4 components, and the obtained alkylation oil had a dry point of 199° C., an RON value of 95.0 and an MON value of 92.0.

Comparative Example 3

This comparative example illustrates the alkylation process and apparatus using concentrated sulfuric acid as the alkylation catalyst.

The same procedure was performed according to Example 1, except that no internal flow disturbance component was provided in the z reaction zone.

The mixing intensities of the x reaction zone and the y reaction zone were 275 μm and 98 μm respectively, examined as the average droplet diameter.

The alkylation reaction product was distilled to remove C4 components, and the obtained alkylation oil had a dry point of 198° C., an RON value of 95.6 and an MON value of 92.3.

Comparative Example 4

This comparative example illustrates the alkylation process and apparatus using concentrated sulfuric acid as the alkylation catalyst.

The same procedure was performed according to Example 1, except that an internal flow disturbance component was provided in the z reaction zone, but the mixing intensity of the z reaction zone was larger than the mixing intensity of the x reaction zone.

The inner diameter of the z reaction zone was 40 mm, and SX type static flow disturbance component was used. The mixing intensities of the x reaction zone, the y reaction zone and the z reaction zone were 275 μm, 98 μm and 210 μm respectively, examined as the average droplet diameter.

The alkylation reaction product was distilled to remove C4 components, and the obtained alkylation oil had a dry point of 197° C., an RON value of 95.7 and an MON value of 92.5.

Example 2

This example illustrates the alkylation process and apparatus using concentrated sulfuric acid as the alkylation catalyst.

Figure 3:
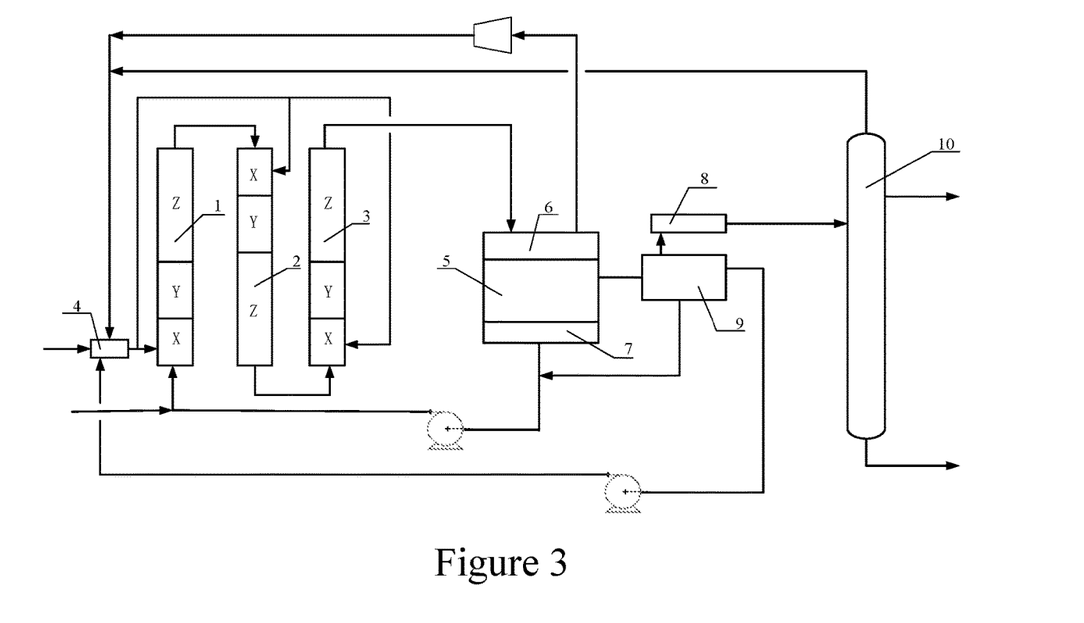
FIG. 3 is a schematic diagram of an alkylation reaction system according to the present invention, which is exemplified by three reactors. In the figure, 1 is a first reactor, 2 is a second reactor, 3 is a third reactor, 4 is a raw material mixer, 5 is a self-vaporization separator, 6 is a coalescing internal member, 7 is an acid hydrocarbon phase homogenizer, 8 is a precise coalescer, 9 is a preliminary acid-hydrocarbon separator, and 10 is a deisobutanizer.

The alkylation reaction was performed in three reactors connected in series, the three reactors were connected in an N-type manner, and x, y and z reaction zones were arranged in each of three reactors (the schematic diagram of the reactor arrangement was shown in FIG. 2, and the schematic diagram of the reaction system was shown in FIG. 3).

The inner diameter of the x reaction zone of each reactor was 40 mm, and SK type static flow disturbance component was used;

The inner diameter of the y reaction zone of each reactor was 25 mm, and Toray Hi-Type static flow disturbance component was used;

The inner diameter of the z reaction zone of each reactor was 100 mm, and SL type static flow disturbance component was used;

Under the conditions that the inlet temperature for the first reactor was −1.0° C. and the flow rate of the recycled acid was 1.2 m3/h, the mixing intensities of the x reaction zone, the y reaction zone and the z reaction zone of each reactor were 175 μm, 88 μm and 1228 μm respectively, examined as the average droplet diameter.

An alkylation catalyst concentrated sulfuric acid and a recycled acid were pumped into the main flow channel of the x reaction zone of the first reactor through the recycled acid pump, and mixed with the reaction raw material, the inlet temperature was −1.0° C., the acid hydrocarbon phases in the x reaction zone and the y reaction zone of the first reactor were subjected to intensive mixing action, and the mixed materials resided in the x reaction zone and the y reaction zone for 1.5 seconds to allow alkene in the feed to be subjected to rapid dispersion and reaction. The reacted material was sent to the z reaction zone and resided for 3.0 minutes for reaction. The reaction stream flowed through the second reactor and the third reactor in sequence, and the reaction effluent from the z reaction zone of the third reactor was sent to the self-vaporization separator. A coalescing internal member was provided at the middle upper part of the self-vaporization separator to provide a place for vaporizing butane and separating a reaction product from an acid phase. The pressure was gradually reduced along with the reaction effluent passing through the coalescence filler. A part of isobutane was vaporized to take away the reaction heat timely; an acid-hydrocarbon phase homogenizer was arranged at the lower part of the self-vaporization separator to ensure the stable operation of the apparatus. A majority of the acid phase separated from the self-vaporization separator was pumped back to the main flow channel of the x reaction zone of the first reactor via the recycled acid pump. The gas phase component (mainly isobutane) from the upper part of the self-vaporization separator was compressed and condensed to be used as isobutane refrigerant. The pressure of the vaporization separator was controlled to be about 0.02 MPa, and the hydrocarbon phase separated from the self-vaporization separator was sent to the preliminary acid-hydrocarbon separator. The acid phase from the lower part of the preliminary acid-hydrocarbon separator was returned to the x reaction zone of the first reactor. A majority of the hydrocarbon phase from the middle upper part of the preliminary acid-hydrocarbon separator was returned as the recycled hydrocarbon to the raw material mixer. A minority of the hydrocarbon phase separated from the top of the preliminary acid-hydrocarbon separator was subjected to a further precision coalescence and then fed to the deisobutanizer. The gas phase isobutane separated from the top of the deisobutanizer was condensed and then returned to the reaction raw material mix. Normal butane was withdrawn from the middle upper part of the deisobutanizer, and the alkylation product was withdrawn from the bottom of the deisobutanizer.

The alkylation reaction product was distilled to remove C4 components, and the obtained alkylation oil had a dry point of 189° C., an RON value of 96.8 and an MON value of 93.4.

Example 3

This example illustrates the alkylation process and apparatus using trifluoromethanesulfonic acid as the alkylation catalyst.

This example was identical to Example 2, i.e. the alkylation reaction was also carried out in three reactors connected in series, in each of which three reaction zones x, y and z were provided, except that concentrated sulfuric acid and trifluoromethanesulfonic acid were used as alkylation catalysts;

The inner diameter of the x reaction zone of each reactor was 40 mm, and SV type static flow disturbance component was used;

The inner diameter of the y reaction zone of each reactor was 30 mm, and SV type static flow disturbance component was used;

The inner diameter of the z reaction zone of each reactor was 100 mm, and SK type static flow disturbance component was used;

The mixing intensities of the x reaction zone, the y reaction zone and the z reaction zone of each reactor were 275 μm, 182 μm and 1367 μm respectively, examined as the average droplet diameter.

The alkylation catalyst was concentrated sulfuric acid and trifluoromethanesulfonic acid (concentrated sulfuric acid: trifluoromethanesulfonic acid=3:1, volume ratio).

The alkylation reaction product was distilled to remove C4 components, and the obtained alkylation oil had a dry point of 196° C., an RON value of 96.3 and an MON value of 93.0.

Examples 4 to 6

Examples 4-6 were identical to Example 2 in the mixing reactor settings and reaction parameters, except for the type of the added auxiliary agents of the catalysts.

This example was identical to Example 2, i.e. the alkylation reaction was also carried out in three reactors connected in series, in each of which three reaction zones x, y and z were provided.

The inner diameter of the x reaction zone of each reactor was 40 mm, and SK type static flow disturbance component was used;

The inner diameter of the y reaction zone of each reactor was 25 mm, and Toray Hi-Type static flow disturbance component was used;

The inner diameter of the z reaction zone of each reactor was 100 mm, and SL type static flow disturbance component was used;

The mixing intensities of the x reaction zone, the y reaction zone and the z reaction zone of each reactor were 175 μm, 88 μm and 1228 μm respectively, examined as the average droplet diameter.

The auxiliary agents were butyl sulfate and hexyl sulfate (mass ratio of 1:2), butyl sulfate and hexyl sulfate (mass ratio of 1:1), and propyl sulfite respectively, the auxiliary agents comprised 0.025% of the alkene feed.

The alkylation reaction products obtained in Examples 4-6 were distilled to remove C4 components. The properties of the obtained alkylation oils are shown in Table 1, while the properties of the alkylation oil in which no auxiliary agent was involved of Example 2 is also shown in Table 1.

TABLE 1

| Examples | Auxiliary agent | Addition amount (weight %) | Alkylation oil | | |
|---|---|---|---|---|---|
| | | | Dry Point | RON | MON |
| 4 | Butyl sulfate and hexyl sulfate (mass ratio of 1:2) | 0.02 | 187 | 97.0 | 93.6 |
| 5 | Butyl sulfate and hexyl sulfate (mass ratio of 1:1) | 0.02 | 185 | 97.2 | 93.7 |
| 6 | Propyl Sulfite | 0.02 | 188 | 96.9 | 93.5 |
| 2 | 0 | 0 | 189 | 96.8 | 93.4 |

As can be seen from Table 1, the reaction result of using the concentrated sulfuric acid and the mixture of butyl sulfate and hexyl sulfate (mass ratio 1:1) is better than that of the concentrated sulfuric acid and the mixture of butyl sulfate and hexyl sulfate (mass ratio 1:2); the reaction result of using the concentrated sulfuric acid and the mixture of butyl sulfate and hexyl sulfate (mass ratio 1:2) is better than that of the concentrated sulfuric acid and the propyl sulfite auxiliary agent, and; the reaction result of using the concentrated sulfuric acid and the propyl sulfite auxiliary agent is better than that of the concentrated sulfuric acid without the addition of the auxiliary agent.

Example 7

This example illustrates the alkylation process and apparatus using concentrated sulfuric acid as the alkylation catalyst.

The alkylation reaction was carried out in four reactors connected in series, four reactors were connected in an M-type manner, and three reaction zones x, y and z were provided in each of said four reactors.

The inner diameter of the x reaction zone of each reactor was 40 mm, and SK type static flow disturbance component was used;

The inner diameter of the y reaction zone of each reactor was 25 mm, and Toray Hi-Type static flow disturbance component was used;

The inner diameter of the z reaction zone of each reactor was 100 mm, and SL type static flow disturbance component was used;

Under the conditions that the medium temperature was −1.0° C. and the flow rate of the recycled acid was 1.2 m3/h, the mixing intensities of the x reaction zone, the y reaction zone and the z reaction zone of each reactor were 175 μm, 88 μm and 1228 μm respectively, examined as the average droplet diameter.

An alkylation catalyst concentrated sulfuric acid and a recycled acid were pumped into the main flow channel of the x reaction zone of the first reactor through the recycled acid pump, and mixed with the reaction raw material, the reaction temperature was controlled to be −1.0° C., the acid hydrocarbon phases in the x reaction zone and the y reaction zone of the first reactor were subjected to intensive mixing action, and the mixed materials resided in the x reaction zone and the y reaction zone for 1.5 seconds to allow alkene in the feed to be subjected to rapid dispersion and reaction. The reacted material was sent to the z reaction zone and resided for 3.0 minutes for reaction. The reaction temperature was controlled to be −1° C. The reaction stream flowed through the second reactor, the third reactor, and the fourth reactor in sequence, and the reaction effluent from the z reaction zone of the fourth reactor was sent to the self-vaporization separator. A coalescing internal member was provided at the middle upper part of the self-vaporization separator to provide a place for vaporizing butane and separating a reaction product from an acid phase. The pressure was gradually reduced along with the reaction effluent passing through the coalescence filler. A part of isobutane was vaporized to take away the reaction heat timely; an acid-hydrocarbon phase homogenizer was arranged at the lower part of the self-vaporization separator to ensure the stable operation of the apparatus. A majority of the acid phase separated from the self-vaporization separator was pumped back to the main flow channel of the x reaction zone of the first reactor via the recycled acid pump. The gas phase component (mainly isobutane) from the upper part of the vaporization separator was compressed and condensed to be used as isobutane refrigerant. The pressure of the vaporization separator was controlled to be about 0.02 MPa, and the hydrocarbon phase separated from the vaporization separator was sent to the preliminary acid-hydrocarbon separator. The acid phase from the lower part of the preliminary acid-hydrocarbon separator was returned to the x reaction zone of the first reactor, and a majority of the hydrocarbon phase from the middle upper part of the preliminary acid-hydrocarbon separator was returned as the recycled hydrocarbon to the raw material mixer. A minority of the hydrocarbon phase separated from the top of the preliminary acid-hydrocarbon separator was subjected to a further precision coalescence and then fed to the deisobutanizer. The gas phase isobutane separated from the top of the deisobutanizer was condensed and then returned to the reaction raw material mix, normal butane was withdrawn from the middle upper part of the deisobutanizer, and the alkylation product was withdrawn from the bottom of the deisobutanizer.

The alkylation reaction product was distilled to remove C4 components, and the obtained alkylation oil had a dry point of 188° C., an RON value of 96.9 and an MON value of 93.5.

The above description is only a preferred embodiment of the present invention, but the scope of the present invention is not limited thereto, and any changes or substitutions that can be easily conceived by those skilled in the art within the technical scope of the present invention are also within the scope of the present invention. Therefore, the protection scope of the present invention should be subject to the protection scope of the claims.

The invention claimed is:

1. An alkylation reaction apparatus, comprising n reactors, wherein m reactors among the n reactors, including a first reactor that are those having each comprises three reaction zones, said three reaction zones being an x reaction zone, a y reaction zone, and a z reaction zone arranged in a direction along a flow direction of an alkylation reaction streams, and
wherein the y reaction zone has a mixing intensity greater than a mixing intensity of the x reaction zone, and the mixing intensity of the x reaction zone is greater than a mixing intensity of z reaction zone, wherein n≥1 and n≥m.

2. The apparatus of claim 1, wherein n is 2, 3, 4, 5, 6, 7, or 8.

3. The apparatus according to claim 1, wherein the X reaction zone, the y reaction zone, and the z reaction zone have inner diameters of Rx, Ry, and Rz, respectively.

4. The apparatus according to claim 1, wherein at least one of the x reaction zone, the y reaction zone, and the z reaction zone is provided with one or more flow disturbance component.

5. The apparatus according to claim 1, wherein said n reactors are connected in series and/or in parallel.

6. An alkylation reaction system comprising an alkylation reaction unit, a compression refrigeration unit, a reaction effluent refining unit, and a product fractionation unit, wherein the alkylation reaction unit comprises the alkylation reaction apparatus according to claim 1.

7. The reaction system according to claim 6, wherein,
the alkylation reaction apparatus is provided with a mixer for receiving a diluted alkylation reaction raw material, wherein the diluted alkylation reaction raw material is obtained by mixing an alkylation reaction raw material with an isobutane refrigerant obtained from the compression refrigeration unit, a recycled isobutane obtained from the product fractionation unit and a recycled hydrocarbon obtained from the reaction effluent refining unit;
a reaction effluent is subjected to a preliminary separation of acid and hydrocarbon in the reaction effluent refining unit, and a majority of a resulting hydrocarbon phase is used as the recycled hydrocarbon; and
a product fractionation unit comprises at least one deisobutanizer, in which isobutane in the hydrocarbon phase of the reaction effluent is removed, and a recycled isobutane, normal butane and an alkylation product are respectively obtained from a top of the deisobutanizer, a middle upper part of the deisobutanizer, and a bottom of the deisobutanizer.

8. The reaction system according to claim 6, wherein the reaction effluent refining unit comprises a self-vaporization separator and a preliminary acid-hydrocarbon separator,
wherein a coalescing internal member is arranged at an upper part of the self-vaporization separator for vaporizing butane and separating a reaction product from an acid phase, and an acid-hydrocarbon phase homogenizer is arranged at a lower part of the self-vaporization separator, and
where the preliminary acid-hydrocarbon separator is used for performing a primary separation of acid and hydrocarbon, a majority of the separated hydrocarbon phase is recycled, and a minority of the hydrocarbon phase is optionally subjected to a further coalescence-deacidification separation.

9. The reaction system according to claim 6, further comprises an alkylation reaction raw material pretreatment unit in which butadiene, light hydrocarbons, oxygen-containing compounds and water are removed from the alkylation reaction raw material.

10. The apparatus of claim 2, wherein n is 3 or 4, m is 2 or 3.

11. The apparatus according to claim 4, wherein the ratio of the inner diameter of the z reaction zone to the inner diameter of the x reaction zone to the inner diameter of the y reaction zone is Rz reaction zone: Rx reaction zone: Ry reaction zone=(2-5):(1.1-1.8):1.

12. The apparatus according to claim 4, wherein the internal flow disturbance component is a static flow disturbance component or a dynamic flow disturbance component.

13. The apparatus according to claim 12, wherein the static flow disturbance component is selected from CompaX Mixer, SMI Mixer, KVM Mixer, SMV Mixer, SMX plus Mixer, SMXL Mixer, SMR Mixer, SMX Mixer, SMR Reactor, Contour Mixer, SMF Mixer, Polygard Mixer, KM Mixer, KMX-V Mixer, HEV Mixer, UltraTab Mixer, WVM Mixer, SV, SH, SK, SX, SL, and Toray Hi-Type.

14. The apparatus according to claim 5, wherein n=3, m=3 or 2, the reactors are connected in series in an N-type manner; or n=4, m=4, or 3, or 2, the reactors are connected in series in an M-type manner.

15. A liquid acid catalyzed alkylation reaction process, wherein the alkylation reaction of isobutane with a C3-C5 alkene fraction is carried out in the presence of a liquid acid in n reactors, and a inlet temperature of a first reactor amongst said n reactors is −10° C. to 20° C.,
    m reactors among said n reactors, including the first reactor, are each provided with an x reaction zone, a y reaction zone and a z reaction zone;
    a diluted alkylation reaction raw material is distributed to said m reactors,
    in each of said m reactors, an alkylation reaction stream firstly flows into the x reaction zone and then successively flows through the y reaction zone and the z reaction zone, and a mixing intensity of the y reaction zone is greater than a mixing intensity of the x reaction zone, which is greater than a mixing intensity of the z reaction zone, wherein n≥1 and n≥m;
    the reaction stream has a residence time in the x reaction zone of 0.01-10 seconds, a residence time in they reaction zone of 0.01-10 seconds, and a residence time in the z reaction zone of 0.1-15 minutes.

16. The reaction process according to claim 15, wherein the diluted alkylation reaction raw material comprises a recycled isobutane, an isobutane refrigerant, an optionally pretreated alkylation reaction raw material, and a recycled hydrocarbon, and a molar ratio of alkane to alkene in the diluted alkylation reaction raw material is 10-300:1.

17. The reaction process according to claim 15, wherein:
    a reaction effluent obtained from an outlet of the nth reactor is depressurized to 0.005-0.18 MPa by a coalescing internal member in a self-vaporization separator, so that a part of C4 alkanes in the reaction effluent is vaporized,
    gas phase components from the reaction effluent are separated, compressed and refrigerated to obtain an isobutane refrigerant, the remainder of the reaction effluent is separated into an acid phase and a hydrocarbon phase in a lower part of the self-vaporization separator, and the acid phase is recycled back to the x reaction zone of the first reactor, a majority of the hydrocarbon phase is sent to a raw material mixer, and a minority of the hydrocarbon phase is sent to an optional precision coalescer to further remove acid and acid esters in the hydrocarbon phase;
    wherein isobutane in the hydrocarbon phase of the reaction effluent is removed in a deisobutanizer, and the recycled isobutane, normal butane and an alkylation product are obtained from a top of the deisobutanizer, a middle upper part of the deisobutanizer, and a bottom of the deisobutanizer, respectively.

18. The process according to claim 15, wherein in the x reaction zone and in the y reaction zone, the pressure drop is 0.05-0.5 MPa, and in the z reaction zone, the pressure drop is 0.001-0.1 MPa.

19. The process according to claim 15, wherein the liquid acid comprising a concentrated sulfuric acid
    and optionally an auxiliary agent, wherein, when the auxiliary agent is present, has a weight percentage of 0.001-0.1% by weight of the C3-C5 alkene fraction, and
    the auxiliary agent is sulfurous acid lower carbon ester or sulfuric acid lower carbon ester.

20. The reaction process according to claim 15, wherein the diluted alkylation reaction raw material is equally distributed to said m reactors, or is distributed to said m reactors in a gradually decreasing manner in the order of the reaction streams in the reactors.

* * * * *